(12) United States Patent
Goeke et al.

(10) Patent No.: US 10,343,971 B2
(45) Date of Patent: Jul. 9, 2019

(54) CROTONATES HAVING USE IN PERFUMERY

(71) Applicant: GIVAUDAN SA, Vernier (CH)

(72) Inventors: Andreas Goeke, Winterthur (CH); Felix Flachsmann, Duebendorf (CH); Dominique Lelievre, Kindhausen (CH); Andreas Natsch, Uetikon (CH); Francis Voirol, Frauenfeld (CH); Yue Zou, Jiangsu (CN); Thierry Granier, Duebendorf (CH)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 16/071,739

(22) PCT Filed: Feb. 15, 2017

(86) PCT No.: PCT/EP2017/053414
§ 371 (c)(1),
(2) Date: Jul. 20, 2018

(87) PCT Pub. No.: WO2017/140733
PCT Pub. Date: Aug. 24, 2017

(65) Prior Publication Data
US 2019/0023643 A1 Jan. 24, 2019

(30) Foreign Application Priority Data

Feb. 16, 2016 (WO) ................ PCT/CN2016/073855

(51) Int. Cl.

| C07C 69/608 | (2006.01) |
|---|---|
| C07C 229/04 | (2006.01) |
| C07C 323/52 | (2006.01) |
| A61Q 13/00 | (2006.01) |
| A61K 8/37 | (2006.01) |
| A61K 8/46 | (2006.01) |
| C07C 69/533 | (2006.01) |
| C07C 69/56 | (2006.01) |

(52) U.S. Cl.
CPC .............. *C07C 69/608* (2013.01); *A61K 8/37* (2013.01); *A61K 8/46* (2013.01); *A61Q 13/00* (2013.01); *C07C 69/533* (2013.01); *C07C 69/56* (2013.01); *C07C 229/04* (2013.01); *C07C 323/52* (2013.01); *C07C 2601/08* (2017.05); *C07C 2601/14* (2017.05); *C07C 2601/16* (2017.05)

(58) Field of Classification Search
CPC . A61K 8/37; A61K 8/46; A61Q 13/00; C07C 69/533; C07C 69/56; C07C 229/04; C07C 2601/08; C07C 2601/14; C07C 2601/16; C07C 69/608; C07C 323/52
See application file for complete search history.

(56) References Cited

U.S. PATENT DOCUMENTS

| 4,198,309 A | 4/1980 | Mookherjee et al. |
| 4,226,892 A | 10/1980 | Kovats et al. |
| 5,087,612 A | 2/1992 | Chapuis |

FOREIGN PATENT DOCUMENTS

| DE | 2659149 | * 7/1978 | ............. C07C 69/24 |
| DE | 2659149 A1 | 7/1978 | |

OTHER PUBLICATIONS

International Search Report and Written Opinion of the International Searching Authority for corresponding application PCT/EP2017/053414 dated May 4, 2017.
J.L. Lewis, "Comparative Localization of Carboxylesterase in F344 Rat, Beagle Dog, and Human Nasal Tissue", The Anatomical Record, vol. 239, pp. 55-64, 1994.
International Search Report and Written Opinion of the International Searching Authority for corresponding priority application PCT/CN2016/073855 dated Nov. 22, 2016.
A. Nagashima, et al., "Enzymatic Conversion of Odorants in Nasal Mucus Affects Olfactory Glomerular Activation Patterns and Odor Perception", The Journal of Neuroscience, 2010; 30(48); pp. 16391-16398.
A. Natsch, et al., "LC-MS-Based Characterization of the Peptide Reactivity of Chemicals to Improve the In Vitro Prediction of the Skin Sensitization Potential", Toxicological Sciences, 106(2), pp. 464-478, 2008.
N. Thiebaud, Odorant Metabolism Catalyzed by Olfactory Mucosol Enzymes Influences Peripheral Olfactory Responses in Rats, Plos One, www.plosone.org, vol. 8, issue 3, pp. 1-13, 2013.
"OECD Guidline for the Testing of Chemicals", OECD/OCDE, TG 442C, pp. 1-19, 2015.

(Continued)

*Primary Examiner* — Rosalynd A Keys
(74) *Attorney, Agent, or Firm* — Norris McLaughlin PA

(57) ABSTRACT

A compound of formula I

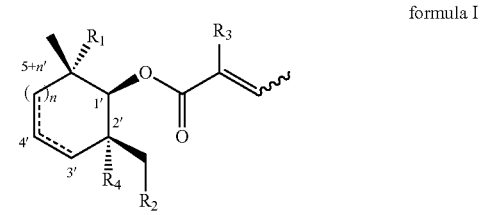

formula I wherein $R_1$, $R_2$, $R_3$ and $R_4$ can be independently selected from H or Me,
n=0, 1,
the dotted lines are indicating single bonds, or in case n=0 an isolated double bond at position 3', or in case n=1 an isolated double bond at position 3' or 4',
and the wavy bond is indicating an unspecified configuration of the adjacent double bond. Said compounds, as well as precursors capable to generate said compounds, are useful as fragrance ingredients.

8 Claims, 3 Drawing Sheets

(56) References Cited

OTHER PUBLICATIONS

"In Vitro Skin Sensitisation Assays Addressing the AOP Key Event on Keratinocyte Activation", Key Event Based Test Guideline 442D, OECD/OCDE, 442D, pp. 1-51, 2018, http://www.oecd.org.
R. Emter, et al., "Perfomance of novel Keratinocyte-based reporter cell line to screen skin sensitizers in vitro", Elsevier Inc., Toxicology and Applied Pharmacology, 245 (210) pp. 281-290, 2010.
T. Ohkuma, et al., "Stereoselective Hydrogenation of Simple Ketones Catalyzed by Ruthenium (II) Complexes", J. Org. Chem., Americal Chemical Society, 61, pp. 4872-4873, 1996.

* cited by examiner

CROTONATES HAVING USE IN PERFUMERY

This is an application filed under 35 USC 371 based on PCT/EP2017/053414, filed 15 Feb. 2017, which in turn is based on PCT/CN2016/073855 filed 16 Feb. 2016. The present application claims the full priority benefit of these prior applications and herein incorporates by reference the full disclosures of these prior applications.

This invention relates to novel organic compounds, a method of preparing said compounds and their use as fragrance ingredients. The invention also relates to perfume compositions and to articles, such as fine fragrances or consumer product compositions perfumed by the compounds or the perfume compositions containing said compounds.

The compounds (2E)-1-(2',6',6'-trimethylcyclohex-2'-en-1'-yl)but-2-en-1-one, (2E)-1-(2',6',6'-trimethylcyclohex-1'-en-1'-yl)but-2-en-1-one, (2E)-1-(2',6',6'-trimethylcyclohex-3'-en-1'-yl)but-2-en-1-one and (2E)-1-(2',6',6'-trimethylcyclohexa-1',3'-dien-1'-yl)but-2-en-1-one, commercially available as Damascone Alpha™, Damascone Beta™, Damascone Delta™ and Damascenone™, are highly desirable fragrance materials, especially where fruity or floral notes are desired. They are described, for example, in U.S. Pat. Nos. 4,198,309 and 4,226,892.

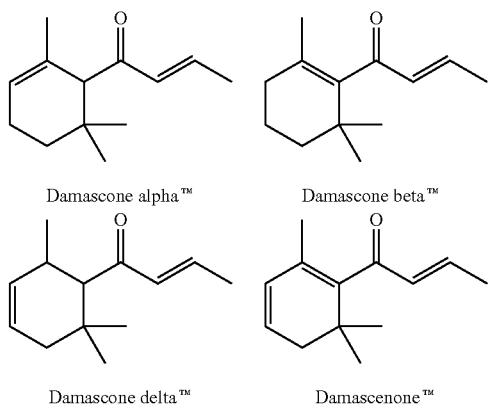

Damascone alpha™  Damascone beta™
Damascone delta™  Damascenone™

However, these materials have proved to be sensitizing in the human repeat-insult patch test (HRIPT) at ≤500 µg/cm² which may give a classification as skin sensitizers of Sub-category 1A in the global harmonized system, leading to some restrictions in their uses in both fine fragrances and consumer product perfume formulations.

Crotonic acid esters of substituted cyclohexanol or cyclohexenol have valuable fruity notes related to odors of strawberry, raspberry apple and plum. Several examples of such compounds are described in DE2659149. However, having also some off-odour notes, these materials have not been commercialised.

Surprisingly, it was now found that the perfumistic benefit of such crotonic acid esters depends on their stereochemistry: Crotonates of formula I can deliver fresh, fruity and floral impressions similar to the Damascones while having the benefit of being significantly less skin sensitizing than these compounds.

Figure 1:
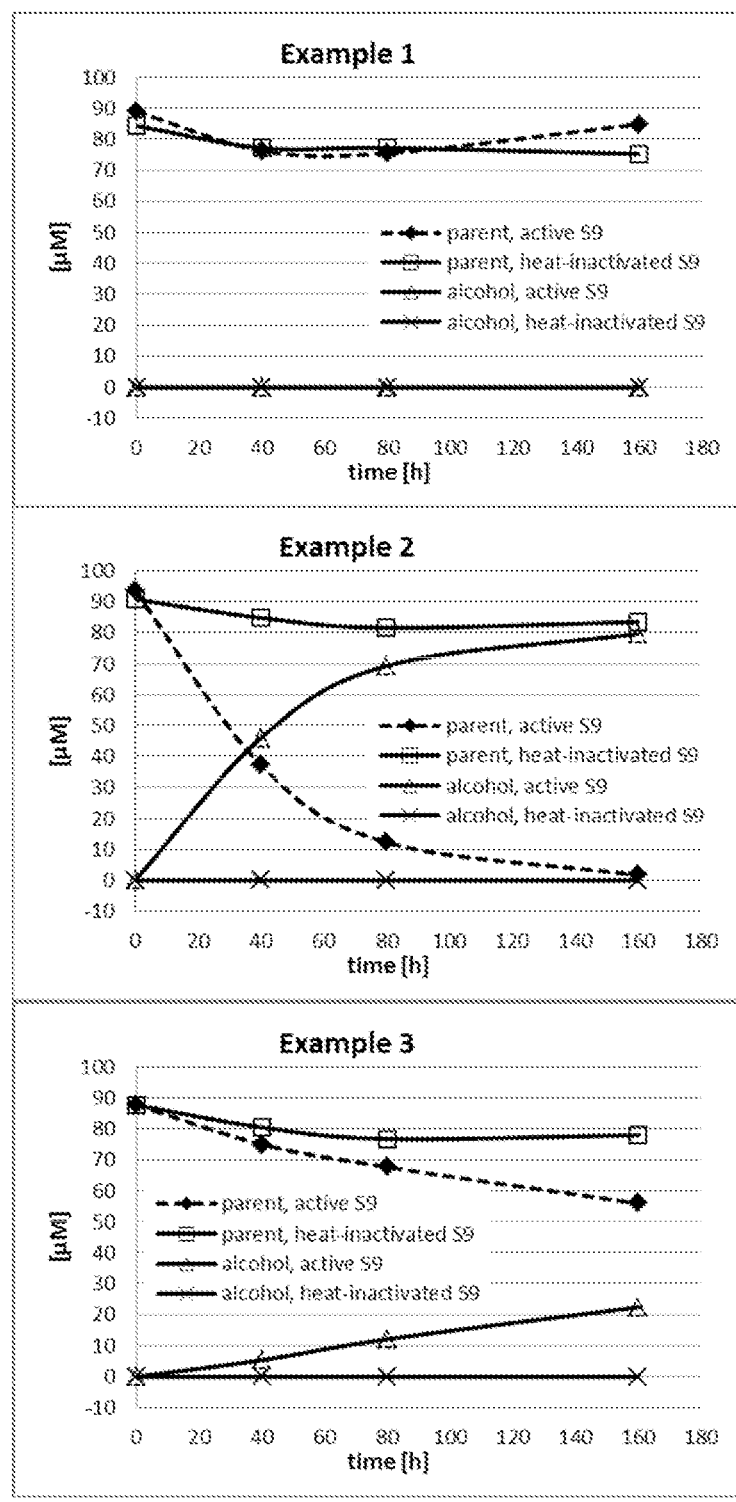
FIG. 1 depicts the enzymatic stability in human liver S9 fractions of the compounds of example 1-3.

So in a first aspect of the invention, a series of 5- or 6-membered cycloalkyl- or cycloalkenyl crotonates according to formula I is provided

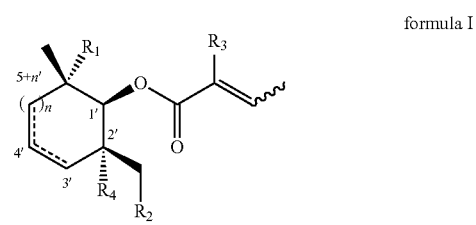

formula I wherein $R_1$, $R_2$, $R_3$ and $R_4$ can be independently selected from H or Me, n=0, 1, the dotted lines are indicating single bonds, or in case n=0 an isolated double bond at position 3', or in case n=1 an isolated double bond at position 3' or 4', the wavy bond is indicating an unspecified configuration of the adjacent double bond, and the substituents at the ring system are having an all-syn relationship. Those isomers with an all-syn relationship are having the pleasant sought-after fruity odor, while other diastereoisomers without an all-syn relationship may produce off-odors which prohibit the use of these diastereomeric crotonates in perfumery.

In general, formula I is indicating the relative but not the absolute configuration at the ring system, as indicated by "*". Therefore, all compounds of the present invention are to be understood as mixtures of enantiomers, unless otherwise stated. Some of the compounds are achiral meso compounds with a pseudoasymmetric centre at position 1' of the ring system, which is indicated by a small s* or r*.

In the compounds of formula I, the double bond of the crotonate residue is not specified, so the double bond may be present either in E- or in Z-configuration, or the compound might be a mixture of E- and Z-isomers.

According to the invention, compounds of formula I possess an all-syn relationship or an all-syn configuration, when the crotonate residue at position 1' of the ring system and the alkyl groups at both adjacent positions 2' and (5+n)' are pointing to the same side of the ring system. In other words, the three vicinal substituents at the 5- or 6-membered ring—an alkyl substituent at position 2', a crotonate residue at position 1' and a further alkyl substituent at position (5+n)', are all in syn-position to each other. For a 5-membered ring (n=0), these are the vicinal substituents at positions 1', 2' and 5', and for a 6-membered ring (n=1), these are the vicinal substituents at positions 1', 2' and 6'. In case that there are two geminal alkyl substituents at positions 2' and/or (5+n)', one of these two geminal alkyl substituents is automatically in syn relation to the crotonate residue at position 1'.

In contrast, the non all-syn configured crotonates do not have said three vicinal substituents pointing to the same side of the ring system.

The off-odor formation observed for the non all-syn configured crotonates of formula I have surprisingly been found to be associated with a lower stability towards enzymatic hydrolysis of diastereomers lacking the all-syn configuration.

It is long known that enzymes in the mucus of the nasal cavity can metabolize odorants, for instance, they can enzymatically hydrolyse esters leading to changed odor impression (N. Thiebaud, S. Veloso Da Silva, I. Jakob, et al., PLoS One 2013, 8; A. Nagashima, K. Touhara, J Neurosci 2010, 30.)

It was now surprisingly found, that the adulterated odor impression or off-odor formation of crotonates is directly proportional to the ability of enzymatic hydrolysis. Without wishing to be bound to theory, the crotonic acid formed by enzymatic hydrolysis in the olfactory bulb is generating the off-odor which hampered commercial use of diastereomeric mixtures of substituted cyclic crotonates. The surprisingly high stability of the all-syn configured crotonates towards enzymatic hydrolysis reduces or even inhibits off-odor formation related to release of crotonic acid. So the enzymatic hydrolysis of all-syn configured crotonates is slower than that of the corresponding non all-syn configured isomers.

In one aspect of the invention, the compound of formula I is provided in highly enriched or essentially pure form as isomer with all-syn configuration, with low amounts or essentially free of the corresponding isomers with non all-syn configuration. That means that the isomer with all-syn configuration is present in at least 90 weight %, particularly in at least 95 weight %, more particularly in at least 98 weight %, even more particularly in 99 weight % or higher.

In another aspect of the invention, a diastereoisomeric mixture of the crotonates is provided, comprising a relatively high amount of the isomer having an all-syn configuration according to formula I along with other stereoisomers having a non all-syn configuration in lower amounts. That means that the isomer with all-syn configuration is present in at least 80 weight %, particularly in at least 90 weight % or higher.

In a particular aspect of the invention, the compound of formula I having the all-syn-configuration is preferred,

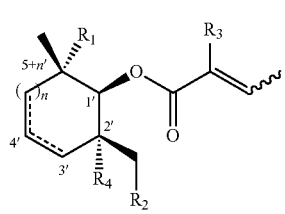

formula I wherein if $R_1$=H then $R_4$=Me, and if $R_1$=Me then $R_4$=H,
$R_2$ and $R_3$ can be independently selected from H or Me, n=0, 1,
the dotted lines are indicating single bonds, or in case n=0 an isolated double bond at position 3', or in case n=1 an isolated double bond at position 3' or 4',
and the wavy bond is indicating an unspecified configuration of the adjacent double bond.

In a further aspect of the invention, the compound of formula I having the all-syn-configuration is preferred,

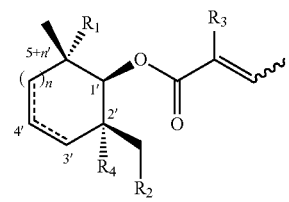

formula I wherein $R_1$ and $R_4$=H,
$R_2$ and $R_3$ can be independently selected from H or Me, n=0, 1,
the dotted lines are indicating single bonds, or in case n=0 an isolated double bond at position 3', or in case n=1 an isolated double bond at position 3' or 4',
and the wavy bond is indicating an unspecified configuration of the adjacent double bond.

In another aspect of the invention, the compound of formula I having the all-syn-configuration is preferred,

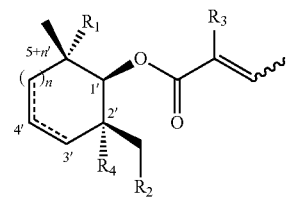

formula I wherein if $R_1$=H then $R_4$=Me, and if $R_1$=Me then $R_4$=H,
$R_2$ and $R_3$ can be independently selected from H or Me, n=1,
the dotted lines are indicating single bonds, or an isolated double bond at position 3', and the wavy bond is indicating an unspecified configuration of the adjacent double bond.

Particular examples of compounds of formula I are
(1s*,2R*,6S*)-2,6-dimethylcyclohexyl (E)-but-2-enoate,
(1s*,2R*,6S*)-2,6-dimethylcyclohexyl (E)-2-methylbut-2-enoate,
(1R*,2S*,6R*)-2-ethyl-6-methylcyclohexyl (E)-but-2-enoate,
(1S*,2S*)-2,6,6-trimethylcyclohex-3-en-1-yl (E)-but-2-enoate,
(1R*,2S*,6R*)-2,6-dimethylcyclohex-3-en-1-yl (E)-but-2-enoate and
(1s*,2R*,5S*)-2,5-dimethylcyclopentyl (E)-but-2-enoate.

Suitable starting compounds for the preparation of compounds of formula I are commercially available cycloalkanones or cycloalkenones, having the desired substituents at the positions vicinal to the carbonyl group. Alternatively, some of the ketones can be obtained from phenols by hydrogenation. The ketones are reduced to the corresponding alcohols, for instance as specified in J. Org. Chem. 1996, 61, 4872-4873. An isomeric mixture is obtained from which the diastereoisomer with all-syn relationship can be isolated. Finally, the alcohol is reacted with crotonyl chloride to yield the compound of formula I.

In a further embodiment, the compound of formula I may be generated by means of a precursor, that is, a compound that, under particular conditions (for example, heat, light, chemical stimulation) will break down to form a compound of formula I. This is particularly useful in some applications, such as laundry or hair care, as the compound can be generated in situ, when its presence is desired.

Therefore, there is also provided a precursor capable of generating a compound of the formula I, the precursor being a compound of the formula II

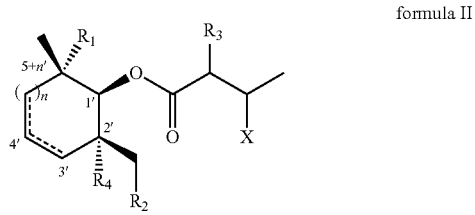

formula II in which $R_1$, $R_2$, $R_3$ and $R_4$ can be independently selected from H or Me, n=0, 1, the dotted lines are indicating single bonds, or in case n=0 an isolated double bond at position 3', or in case n=1 an isolated double bond at position 3' or 4', the substituents at the ring system are having an all-syn relationship, and X is selected from $SR^5$, $NHR^6$ and $NR^6R^7$, $R^5$, $R^6$ and $R^7$ being selected from linear or branched $C_1$-$C_{15}$ alkyl, a $C_3$-$C_8$ cycloalkyl or an aryl substituent, the cycloalkyl and aryl being optionally substituted with linear or branched $C_1$-$C_7$ alkyl groups, or, in the case of $NR^6R^7$, $R^6$ and $R^7$, together with the nitrogen atom to which they are attached, form part of a polymeric entity.

Furthermore, there is also provided a method of providing in a fragrance application a compound of formula I as hereinabove described, comprising
 (i) the preparation of a compound of formula II
 (ii) adding the compound of formula II to an application; and
 (iii) subjecting the application to conditions that will result in the generation of a compound of the formula I.

There is further provided the use of a compound of formula II in a fragrance application for the in situ generation of a compound according to formula I.

In the case of polymeric entities, any such suitable entity is suitable, a typical example being a polyethylene imine. Such materials are readily available commercially, for example the Lupasol™ range of BASF.

The compound of formula II may be prepared by any suitable method known to the art.

The materials and conditions for such a preparation are well known to the art, and only routine, non-inventive experimentation is required to produce a suitable compound. In a typical, non-limiting example, a compound of formula II may be prepared by the reaction of approximately equimolar amounts of a compound of formula I with one of $HSR^5$, $H_2NR^6$, $HNR^6R^7$, preferably at 20-80° C., either neat or in a solvent such as ethanol or toluene, optionally in the presence of an organic base, such as 1,8-diazabicyclo[5.4.0]undec-7-ene (0.5-1.5 equivalents), or an inorganic base, such as potassium carbonate. The product may be isolated by standard workup procedures known to the person skilled in the art of organic synthesis. The compound of formula II may be used in crude form, or it may be purified by standard purification procedures, such as column chromatography or distillation.

The crotonates of formula I are found to be significantly less skin sensitizing than the Damascones. The level of skin sensitization can be reliably and quantitatively measured by the KeratinoSens method, which measures the induction of Nrf2-dependent luciferase in a skin cell line. This test has been adopted as OECD test guideline 442d. Compounds of this invention do not induce the luciferase in this test and are therefore rated as non-sensitizing. Alternatively, the sensitization potential can be quantified by measuring the reactivity of test chemicals with peptides. This approach has been developed as the direct peptide reactivity assay (DPRA) and implemented in OECD test guideline 442c. Modifications of this method which allow for a better quantification of reactivity have been described (A. Natsch, H. Gfeller, Toxicol. Sci. 2008, 106, 464-478). Based on this test, the compounds of this invention have a reactivity which is >100-fold reduced as compared to Damascone delta, confirming that their skin sensitization potential is strongly reduced.

Therefore, in a further aspect of the invention, there is provided a method to impart a fresh, fruity and floral fragrance note having a reduced skin sensitization, by using a compound of formula I in perfume mixtures.

Furthermore, such perfume mixtures containing a compound of formula I are used to perfume consumer products.

The compounds of formula I may be used in fragrance compositions, that is, compositions that provide desirable fragrance, either as stand-alone fragrance providers or incorporated into fragrance applications to provide them with a desirable fragrance. The compounds of formula I may be used individually or in combination with one or more other compounds of formula I. They may be combined in such fragrance compositions with any of the known range of commercially-available fragrance raw materials, either natural or synthetic, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, surfactants and other auxiliary agents commonly used in the art. Examples of suitable diluents include dipropylene glycol (DPG), isopropyl myristate (IPM), triethyl citrate (TEC) and alcohol (e.g. ethanol). These may be used in the normal proportions known to the art.

The following list comprises non-limiting examples of known odorant molecules, which may be combined with the compounds of formula I:

essential oils and extracts, e.g. agarwood oil (white and/or authentic), castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;

aldehydes and ketones, e.g. Azurone® [7-(3-methylbutyl)-1,5-benzodioxepin-3-one], anisaldehyde, α-amylcinnamaldehyde, Cashmeran®, Georgywood™, Hedione®, hydroxycitronellal, Iso E Super®, Isoraldeine®, Kephalis™, Lilial®, maltol, methyl cedryl ketone, methylionone, verbenone, or vanillin;

ether and acetals, e.g. Ambrox®, geranyl methyl ether, rose oxide, or Spirambrene®;

esters and lactones, e.g. benzyl acetate, cedryl acetate, γ-decalactone, Helvetolide®, γ-undecalactone or vetivenyl acetate;

macrocycles, e.g. Ambrettolide, ethylene brassylate or Exaltolide®; and heterocycles, e.g. isobutylchinoline.

The compounds according to formula I may be used in a broad range of fragrance applications, that is, products in which fragrance is desired. Such fragrance applications may be in any field of fine and functional perfumery, such as perfumes, air care products, household products, laundry products, body care products and cosmetics. Non-limiting examples of such products include textile treatment products, ironing aids, laundry detergents, laundry care products, fabric conditioners, cleaning products, in particular, for hard and/or soft surfaces, such as furniture and floor polishes general purpose cleaners, specific cleaners for kitchen and toilet use, disinfectants, room fragrancers and air fresheners, toilet blocks, hair care products, such as shampoos, colourants and conditioners, anti-mould and anti-fungal products, oral care products such as toothpastes, tooth gels and mouthwashes, cosmetics and pharmaceuticals.

Because of the reduced or even totally eliminated tendency for skin sensitisation, the compounds of formula I are particularly effective in fragrance applications that will be in contact with the skin, either of short duration (cleaning materials) or long duration (cosmetics and pharmaceutical preparations).

The fragrance applications may be prepared by mixing the compounds, alone or as part of a fragrance composition, into a fragrance application base, that is, a composition comprising all the ingredients of the desired fragrance application apart from the perfume. These will naturally depend on the nature of the fragrance application but typical non-limiting examples well known to and used by the art include surfactants, detersive agents, abrasive agents, solvents, thinners and diluents, pigments, dyestuffs and other colouring matters, thickeners and rheology modifiers, disinfectants and antimicrobial compounds, extenders and fillers. The proportions that may be used are those well known to the art for each particular use and circumstance.

The compounds can be employed in widely varying amounts, depending upon the specific fragrance application and on the nature and quantity of other odorant ingredients. The proportion is typically from 0.1 to 10 weight percent of the application. In one embodiment, compounds of the present invention may be employed in a fabric softener in an amount of from 0.001 to 0.1 weight percent. In another embodiment, compounds of the present invention may be used in fine perfumery in amounts from 0.01 to 20 weight percent (e.g. up to about 10 weight percent), more preferably between 0.01 and 5 weight percent. However, these values are given only by way of example, since the experienced perfumer may also achieve effects or may create novel accords with lower or higher concentrations.

The compounds of formula I, of fragrance compositions incorporating them, may also be incorporated in perfumed products in entrapped form, that is, entrapped within a suitable entrapment material. Typical examples of entrapment well known to the art include polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like.

The invention is now further described with reference to the following non-limiting examples. These examples are for the purpose of illustration only, and it is understood that variations and modifications can be made by one skilled in the art.

EXAMPLES

Example 1: (1s*,2R*,6S*)-2,6-dimethylcyclohexyl (E)-but-2-enoate

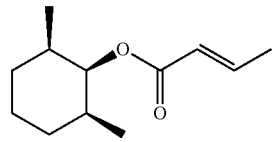

a) Sodium borohydride (18.6 g, 499 mmol) was added portion wise to a solution of 2,6-dimethylcyclohexanone (90.0 g, 713 mmol, mixture of isomers) in methanol (300 ml) at −20° C. After complete addition, the cooling bath was removed and stirred for 1 hour. The reaction mixture was diluted with MTBE (300 ml) and poured into 2M HCl (200 ml). The organic phase was washed with water and (200 ml) and brine (200 ml), dried (MgSO$_4$) and concentrated in vacuo to yield the product as a mixture of diastereomers (82.9 g) as a clear slightly yellow liquid. From 12.0 g of the crude product, (1s*,2R*,6S*)-2,6-dimethylcyclohexanol (3.85 g, 29%) was isolated by chromatography over silica gel (hexane:MTBE=9:1).

b) To a cooled (0° C.) solution of (1s*,2R*,6S*)-2,6-dimethylcyclohexanol (3.00 g, 23.40 mmol) in THF (60 ml) was added a catalytic amount of 1,10-phenanthroline and butyl lithium (14.6 ml, 1.6 M solution in hexane). The color of the solution gradually turned from yellow to brown and the internal temperature rose to 6° C. A solution of crotonyl chloride (3.26 g, 28.10 mmol) in THF (20 ml) was added dropwise while the temperature rose to 30° C. The mixture was stirred for another 15 min at room temperature. Then MTBE (80 ml) and 2M HCl (80 ml) were added. The organic phase was washed with water (80 ml) and brine (80 ml), dried (MgSO$_4$) and concentrated in vacuo. The residue (4.40 g of a yellowish oil) was purified by chromatography over silica gel (hexane:MTBE=99:1) and Kugelrohr distillation (120° C., 0.06 mbar) to yield (1s*,2R*,6S*)-2,6-dimethylcyclohexyl (E)-but-2-enoate (2.1 g, 46%) as a colorless oil.

$^1$H-NMR (400 MHz, CDCl$_3$) δ ppm 6.98 (dq, J=15.6, 6.9 Hz, 1H) 5.88 (dq, J=15.6, 1.71 Hz, 1H) 5.08 (t, J=2.2 Hz, 1H) 1.89 (dd, J=6.8, 1.71 Hz, 3H) 1.71-1.77 (m, 1H) 1.57-1.69 (m, 2H) 1.20-1.46 (m, 5H) 0.83 (d, J=6.8 Hz, 6H). $^{13}$C-NMR (101 MHz, CDCl$_3$) b ppm 166.7 (s) 143.9 (d) 123.1 (d) 76.1 (d) 36.4 (d, 2C) 28.6 (t, 2C) 25.8 (t) 18.3 (q, 2C) 17.9 (q). GC/MS (EI): 110 (M+, —C$_4$H$_6$O$_2$, 32), 109 (13), 95 (36), 69 (100), 55 (14), 41 (23), 32 (16).

Odor: baked apple, pineapple, plum jam, creamy, damascenone

Comparative Example 2: (2R*,6R*)-2,6-dimethylcyclohexyl (E)-but-2-enoate

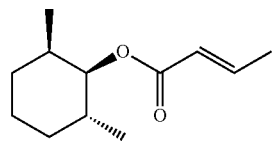

a) In an autoclave, neat 2,6-dimethylcyclohexanone (900 g, 7.13 mol) was hydrogenated over carbonylhydrido(tetrahydroborato)[bis(2-diphenylphosphinoethyl)-amino]ruthenium(II) (Ru-MACHO, CAS 1295649-40-9) (0.5 g) during 3 h at 50 bar and 80° C. The reaction product, consisting of the (1s*,2R*,6S*)— and the (2R*,6R*)-2,6-dimethylcyclohexan-1-ol isomers in a ratio of 67:33, was fractionated over a 100 cm Sulzer column to yield (2R*,6R*)-2,6-dimethylcyclohexanol (41 g, bp. 43° C./5 mbar).

b) (2R*,6R*)-2,6-Dimethylcyclohexyl (E)-but-2-enoate was synthesized from (2R*,6R*)-2,6-dimethylcyclohexanol and (E)-but-2-enoyl chloride in a yield of 68% according to Example 1.

1H NMR (400 MHz, CDCl$_3$) δ ppm 7.28 (s, 1H) 6.98 (dq, J=15.5, 7.0 Hz, 1H) 5.88 (dq, J=15.5, 1.7 Hz, 1H) 4.65 (dd, J=8.1, 3.9 Hz, 1H) 2.06-2.15 (m, 1H) 1.90 (dd, J=7.0, 1.7 Hz, 3H) 1.69-1.77 (m, 1H) 1.41-1.58 (m, 4H) 1.10-1.20 (m, 1H) 0.92 (dd, J=6.8, 2.4 Hz, 6H). 13C NMR (101 MHz, CDCl$_3$) δ ppm 166.2 (s) 143.9 (d) 123.3 (d) 79.2 (d) 31.3 (d) 30.9 (d) 30.5 (t, 2C) 19.8 (t) 17.9 (q) 17.7 (q) 14.3 (q). GC/MS (EI): 110 (M+, —C$_4$H$_6$O$_2$, 53), 109 (5), 95 (76), 69 (100), 82 (8), 81 (8), 55 (10), 41 (29), 39 (17).

Odor: Fruity, metallic, animalic, crotonic

Comparative Example 3: (1r*,2R*,6S*)-2,6-dimethylcyclohexyl (E)-but-2-enoate

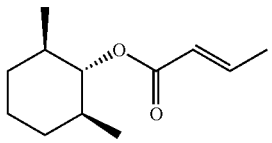

a) A solution of (1s*,2R*,6S*)-2,6-dimethylcyclohexanol (10.0 g, 78 mmol, prepared as described in Example 1, step a) in acetone (100 ml) was cooled to 5° C. and Jones reagent (19.5 ml) was added dropwise (temperature rose to 20° C.). The mixture is stirred for another 30 min, and isopropanol (10 ml) is added dropwise and left stirring for another 10 min. The reaction mixture was diluted with MTBE (150 ml) and poured on 2M NaOH (100 ml). The organic phase was washed with water (100 ml) and brine (2×100 ml), dried (MgSO$_4$) and concentrated in vacuo to afford (2R*,6S*)-2,6-dimethylcyclohexanone (9.0 g, 91%) as a clear colorless liquid.

b) A solution of (2R*,6S*)-2,6-dimethylcyclohexanone (10.0 g, 79 mmol) in methanol (100 ml) was cooled to 5° C. and sodium borohydride (2.10 g, 55.5 mmol) was added in 3 portions (temperature rose to 20° C.). The cooling bath was removed and the mixture stirred for 30 min, diluted with MTBE (150 ml) and poured onto 2M NaOH (100 ml). The organic phase was washed with water (100 ml) and brine (2×100 ml), dried (MgSO$_4$) and concentrated in vacuo to yield a diastereomeric mixture of 2,6-dimethyl cyclohexanols (7.7 g). (1r*,2R*,6S*)-2,6-Dimethylcyclohexanol (1.80 g, 17.7%) was isolated from the mixture by chromatography on silica gel (hexane:MTBE=87:13) and recrystallization as colorless crystals.

c) To a cooled (0° C.) solution of (1r*,2R*,6S*)-2,6-dimethylcyclohexanol (1.80 g, 14.04 mmol) in THF (50 ml) was added a catalytic amount of 1,10-phenanthroline and butyl lithium (8.8 ml, 1.6 M solution in hexane). The color of the solution gradually turned from yellow to brown and the internal temperature rose to 6° C. A solution of crotonyl chloride (1.96 g, 16.85 mmol) in THF (20 ml) was added dropwise while the temperature rose to 20° C. The mixture was stirred for another 15 min at room temperature. Then MTBE (80 ml) and 2M HCl (80 ml) were added. The organic phase was washed with water (80 ml) and brine (80 ml), dried (MgSO$_4$) and concentrated in vacuo. The residue (3.16 g of a yellowish oil) was purified by chromatography over silica gel (hexane:MTBE=99:1) and Kugelrohr distillation (120° C., 0.06 mbar) to yield (1r*,2R*,6S*)-2,6-dimethylcyclohexyl (E)-but-2-enoate (0.71 g, 25%) as a colorless oil.

1H-NMR (400 MHz, CDCl$_3$) δ ppm 7.00 (dq, J=15.4, 6.9 Hz, 1H) 5.89 (dq, J=15.7, 1.7 Hz, 1H) 4.38 (t, J=10.3 Hz, 1H) 1.90 (dd, J=6.9, 1.7 Hz, 3H) 1.72-1.79 (m, 2H) 1.61-1.68 (m, 1H) 1.49-1.61 (m, 1H) 1.22-1.36 (m, 1H) 1.05-1.18 (m, 2H) 0.86 (d, J=6.6 Hz, 6H). $^{13}$C-NMR (101 MHz, CDCl$_3$) 5 ppm 166.7 (s) 144.3 (d) 122.9 (d) 82.6 (d) 37.9 (d, 2C) 33.9 (t, 2C) 25.3 (t) 18.5 (q, 2C) 17.9 (q). GC/MS (EI): 110 (M+, —C$_4$H$_6$O$_2$, 36), 95 (26), 82 (6), 69 (100), 55 (7), 41 (22), 39 (13).

Odor: Fruity metallic, crotonic

Example 4: (1s*,2R*,6S*)-2,6-dimethylcyclohexyl (E)-2-methylbut-2-enoate

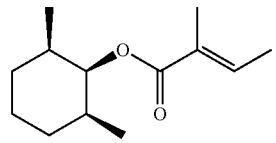

This compound was synthesized from (1s*,2R*,6S*)-2,6-dimethylcyclohexanol and (E)-2-methylbut-2-enoyl chloride in a yield of 68% according to Example 1.

$^1$H-NMR (400 MHz, CDCl$_3$) δ ppm 6.89 (qq, J=7.1, 1.5 Hz, 1H) 5.10 (br s, 1H) 1.88-1.87 (m, 3H) 1.82 (dq, J=7.1, 1.5 Hz, 3H) 1.61-1.69 (m, 2H) 1.22-1.51 (m, 6H) 0.84 (d, J=6.8 Hz, 6H). $^{13}$C-NMR (101 MHz, CDCl$_3$) δ ppm 168.2 (s) 136.5 (d) 128.9 (s) 76.4 (d) 36.5 (d, 2C) 28.8 (t, 2C) 25.9 (t) 18.4 (q) 14.3 (q) 12.2 (q). GC/MS (EI): 110 (M$^+$, —C$_5$H$_8$O$_2$, 43), 109 (7), 101 (8), 95 (32), 83 (100), 69 (14), 55 (38), 41 (12), 39 (8).

Odor: fruity, red fruits

Example 5: (1R*,2S*,6R*)-2-ethyl-6-methylcyclohexyl (E)-but-2-enoate

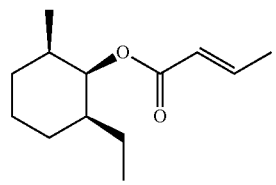

a) A solution of 2-ethyl-6-methylphenol (25 g, 184 mmol) in hexane (20 ml) was hydrogenated in an autoclave over Pd on carbon (10%, 0.2 g) during 48 h at 50 bar and 100° C. The mixture was filtered over a pad of silica gel and concentrated in vacuo to yield 2-ethyl-6-methylcyclohexanone as a slightly turbid oil (24.38 g) which was used directly in the next step.

b) In an autoclave, neat 2-ethyl-6-methylcyclohexanone (24 g, 174 mol) was hydrogenated over carbonylhydrido (tetrahydroborato)[bis(2-diphenylphosphinoethyl)-amino]ruthenium(II) (Ru-MACHO, CAS 1295649-40-9; 10 mg) during 21 h at 50 bar and 80° C. The crude reaction product (21.2 g), consisting of a mixture of isomers, was purified by chromatography (SiO$_2$, hexane:MTBE=87:13) to yield diastereomerically pure (1R*,2S*,6R*)-2-ethyl-6-methylcyclohexan-1-ol (3.71 g, 15%) which was used directly in the next step.

c) (1R*,2S*,6R*)-2-ethyl-6-methylcyclohexan-1-ol (1.75, 12.3 mmol) was esterified according to Example 1b.

(1R*,2S*,6R*)-2-Ethyl-6-methylcyclohexyl (E)-but-2-enoate: $^1$H-NMR (400 MHz, CDCl$_3$) b ppm 6.96 (dq, J=15.4, 6.8 Hz, 1H) 5.86 (dq, J=15.5, 1.7 Hz, 1H) 5.18 (bs, 1H) 1.87 (dd, J=6.8, 1.8 Hz, 3H) 1.49-1.78 (m, 3H) 1.19-1.48 (m, 6H) 1.07-1.16 (m, 1H) 0.87 (d, J=7.3 Hz, 3H), 0.82 (d, J=6.8 Hz, 3H). $^{13}$C-NMR (101 MHz, CDCl$_3$) δ ppm 166.5 (s) 143.9 (d) 123.0 (d) 74.3 (d) 43.6 (d) 36.4 (d) 29.0 (t) 26.6 (t) 25.8 (t) 25.5 (t) 18.4 (q) 17.9 (q) 11.6 (q). GC/MS (EI): 210 (M$^+$, <1), 181 (2), 124 (22), 109 (4), 95 (58), 82 (8), 69 (100), 55 (16), 41 (34), 29 (6).

Odor: fruity, saffron, plum, damascone-like, apple

Example 6a: (1S*,2S*)-2,6,6-Trimethylcyclohex-3-en-1-yl (E)-but-2-enoate and Comparative Example 6b: (1S*,2R*)-2,6,6-trimethylcyclohex-3-en-1-yl (E)-but-2-enoate

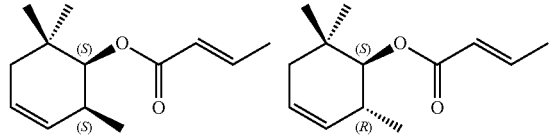

a) A few ml of a solution of (E)-1-chlorobut-2-ene (25.6 g, 282 mmol) in THF (200 ml) were added to magnesium turnings (8.58 g, 353 mmol) in THF (100 ml) under argon atmosphere. After the reaction had started, the rest of the chlorobutene solution was added dropwise. The mixture was allowed to cool to room temperature and a solution of 2,2-dimethylpent-4-enal (40.0 g, 66% solution in toluene, 235 mmol) in THF (50 ml) was added slowly. The mixture was cooled to 0° C. and quenched with aq. NH$_4$Cl (200 ml). The organic layer was separated and the aqueous layer was extracted with ethyl acetate (3×200 mL). The combined organic layers were washed with brine, dried (MgSO$_4$) and concentrated in vacuo. The residue was distilled bulb-to-bulb (0.14 mbar, 140° C.) to yield 20.0 g of 3,5,5-trimethylocta-1,7-dien-4-ol as a colorless oil.

b) To a 250 ml single-neck round-bottomed flask was added above product, dissolved in toluene (20 ml), and Zhan Catalyst-1B (CAS 918870-76-5; 0.346 g, 0.471 mmol) under Ar atmosphere. The reaction was heated to 80° C. for 1 h. Then, the solvent was evaporated and the residue purified by chromatography on silica gel (hexane:MTBE=100:1) and distilled bulb-to-bulb to give 5.0 g of 2,6,6-trimethylcyclohex-3-enol (syn/anti isomers in a ratio of 58:42) as a colorless oil.

c) To a solution of methylmagnesium bromide (7.84 ml, 23.53 mmol) in THF (20 ml) was added 2,6,6-trimethylcyclohex-3-enol (syn/anti isomers in a ratio of 58:42, 3.00 g, 21.4 mmol) dropwise at −10° C. under argon atmosphere. Then, (E)-but-2-enoyl chloride (3.35 g, 32.1 mmol) was added slowly at this temperature. The mixture was stirred for 1 h at room temperature, poured onto water (100 mL) and extracted with MTBE (3×100 mL). The combined organic layers were dried (MgSO$_4$) and concentrated in vacuo. The residue was purified by chromatography (silica gel, hexane:MTBE=100:1) and Kugelrohr distillation to (0.13 mbar, 83° C.) to give (1S*,2S*)-2,6,6-trimethylcyclohex-3-en-1-yl (E)-but-2-enoate (1.00 g 22%) and (1S*,2R*)-2,6,6-trimethylcyclohex-3-en-1-yl (E)-but-2-enoate (0.5 g, 11%), both as colorless oils.

(1S*,2S*)-Isomer: $^1$H NMR (300 MHz, CDCl$_3$) δ ppm 6.96 (dq, J=15.7, 7.0 Hz, 1H) 5.87 (dq, J=15.7, 1.6 Hz, 1H) 5.65 (dddd, J=10.1, 5.0, 2.4, 2.4 Hz, 1H) 5.34 (br d, J=10.1 Hz, 1H) 4.87 (d, J=3.6 Hz, 1H) 2.45-2.56 (m, 1H) 2.08 (br dd, J=17.5, 3.0 Hz, 1H) 1.87 (dd, J=7.0, 1.6 Hz, 3H) 1.68 (br dd, J=17.5, 4.4 Hz, 1H) 0.95 (s, 3H) 0.93 (d, J=7.2 Hz, 3H) 0.87 (s, 3H). $^{13}$C NMR (75 MHz, CDCl$_3$) δ ppm 166.7 (s) 144.4 (d) 128.4 (d) 125.2 (d) 122.9 (d) 77.5 (d) 34.9 (t) 33.5 (s) 31.6 (d) 27.1 (q) 24.9 (q) 17.9 (q) 16.1 (q).

GC/MS (EI): 208 (M$^+$, <1), 140 (42), 122 (27), 107 (31), 91 (6), 69 (100), 55 (5).

(1S*,2R*)-Isomer: $^1$H NMR (300 MHz, CDCl$_3$) δ ppm 7.00 (dq, J=15.3, 6.8 Hz, 1H) 5.89 (dq, J=15.3, 1.5 Hz, 1H) 5.48-5.56 (m, 1H) 5.41 (d, J=9.8 Hz, 1H) 4.70 (d, J=9.4 Hz, 1H) 2.33-2.23 (m, 1H) 2.14-2.04 (m, 1H) 1.90 (dd, J=6.8, 1.5 Hz, 3H) 0.96 (d, J=7.0 Hz, 3H) 0.95 (s, 3H), 0.88 (s, 3H). $^{13}$C NMR (75 MHz, CDCl$_3$) δ ppm 166.6 (s) 144.4 (d) 130.4 (d) 124.6 (d) 122.9 (d) 81.1 (d) 40.2 (t) 34.0 (s) 33.9 (d) 27.2 (q) 20.0 (q) 18.1 (q) 17.9 (q). GC/MS (EI): 208 (M$^+$, <1), 140 (41), 122 (25), 107 (28), 91 (6), 69 (100), 55 (5).

Odor (1S*,2S*)-Isomer: fruity green, damascone, stronger than the (1S*,2R*) derivative Odor (1S*,2R*)-Isomer: weaker, fruity, slightly crotonic Example 7: (1R*,2S*,6R*)-2,6-Dimethylcyclohex-3-en-1-yl (E)-but-2-enoate

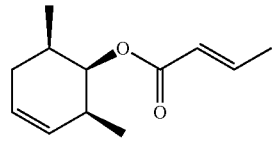

a) Sodium borohydride (0.19 g, 5.13 mmol) was added to a solution of 2,6-dimethylcyclohex-3-enone (0.91 g, 7.33 mmol, mixture of isomers) in methanol (20 ml). The temperature was kept at 30° C. by means of a water bath. After 1 h, the mixture was poured into diluted HCl (20 ml, 2 M) and extracted twice with MTBE (40 ml). The combined organic phases were washed with water (40 ml) and brine (40 ml), dried (MgSO$_4$) and concentrated in vacuo to yield a colorless clear oil (0.41 g) which was purified by chromatography over silica gel (hexane:MTBE=84:16) to afford 0.22 g of a colorless oil from which (1R*,2S*,6R*)-2,6-dimethylcyclohex-3-en-1-ol (0.13 g) solidified in form of colorless crystals which were used directly in the next step.

b) A solution of (1R*,2S*,6R*)-2,6-dimethylcyclohex-3-en-1-ol (0.13 g, 1.30 mmol) and a spatula tip of 1,10-phenantroline in THF (20 ml) were cooled to −10° C. Then, 0.7 ml buthyllithium (1.6M in hexane) were added (the temperature rose to −5° C. and the color changed from yellow to dark brown). The mixture was stirred for 10 min, followed by addition of crotonyl chloride (0.13 g, 1.13 mmol). After completed addition, the cooling bath was removed and the mixture was stirred for 30 min and poured into aq. HCl (20 ml, 2M) and extracted two times with MTBE (20 ml). The organic layer was washed with water (20 ml) and brine (20 ml), dried over MgSO$_4$ and evaporated in vacuo to yield 0.27 g of an clear, yellow liquid which was purified by a flash chromatography over silica gel (hexane/MTBE 50:1) to yield (1R*,2S*,6R*)-2,6-dimethylcyclohex-3-en-1-yl (E)-but-2-enoate (0.11 g, 55%) as a colorless oil.

$^1$H NMR (600 MHz, BENZENE-d$_6$) δ ppm 6.9 (dq, J=15.4, 6.9 Hz, 1H) 5.8 (dq, J=15.4, 1.6 Hz, 1H) 5.7 (ddt, J=10.2, 5.0, 2.6, 2.6 Hz, 1H) 5.3-5.3 (m, 2H) 2.26-2.20 (m, 1H) 1.96-1.89 (m, 1H) 1.82-1.76 (m, 1H) 1.67-1.61 (m, 4H) 1.29 (dd, J=6.8, 1.9 Hz, 3H) 1.0 (d, J=7.2 Hz, 3H) 0.9 (d, J=6.8 Hz, 3H). $^{13}$C-NMR (151 MHz, C$_6$D$_6$) δ ppm 166.2 (s) 144.0 (d) 129.8 (d) 126.1 (d) 123.3 (d) 73.6 (d) 35.5 (d) 32.8 (d) 29.3 (t) 18.3 (q) 17.4 (q) 16.6 (q). GC/MS (EI): 18.3 (q, 2C) 17.9 (q). GC/MS (EI): 194 (M$^+$, 1), 126 (9), 108, (48), 93 (21), 81 (6), 69 (100), 55 (7), 41 (18).

Odor: pleasant apple, plum jam, creamy, damascenone

Example 8: (1s*,2R*,5S*)-2,5-dimethylcyclopentyl (E)-but-2-enoate+stereoisomers

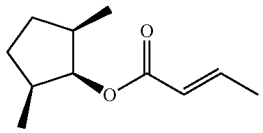

a) Dimethyl carbonate (224.8 g, 2.5 mol) was added to a suspension of sodium hydride (60% in oil, 125 g, 3.11 mol) in THF (500 ml) and the resulting mixture was heated to reflux and treated dropwise within 1.5 h with a solution of 98% pure 2-methyl cyclopentanone (100 g, 1 mol) in THF (500 ml). The resulting mixture was stirred at reflux for 45 min, cooled to 5° C., and treated dropwise within 1 h with an aqueous solution of 3M AcOH (1 l). The mixture was then acidified to pH 1 by addition of conc. HCl. and the resulting mixture was treated with aq. sat. NaCl soln. (0.5 l) and extracted with MTBE (1 l). The water phase was extracted twice with MTBE (0.5 l) and the combined organic phases were washed with brine, dried (MgSO$_4$) and concentrated. The crude product (233 g, yellow oil) was purified by short-path distillation (0.1 mbar; oil bath temperature: 100° C., boiler temp: 85° C., head temp: 80° C.) leading to 3-methyl-2-oxo-cyclopentanecarboxylic acid methyl ester (162 g, quant., colorless oil, ratio of diastereomers=48:52).

b) A mixture of 3-methyl-2-oxo-cyclopentanecarboxylic acid methyl ester (10 g, 0.064 mol), methyl iodide (27.2 g, 0.192 mol), and potassium carbonate (35.4 g, 0.256 mol) in acetone (100 ml) was refluxed for 1 h, cooled to 20° C., poured into 2N HCl/ice and extracted twice with MTBE (100 ml). The combined organic phases were washed with brne, dried (MgSO$_4$), and concentrated affording crude 1,3-dimethyl-2-oxo-cyclopentanecarboxylic acid methyl ester (9.4 g, yellow oil, 89% yield over 2 steps, 1:2 mixture of diastereomers).

c) A mixture of 1,3-dimethyl-2-oxo-cyclopentanecarboxylic acid methyl ester (9.4 g, 0.055 mol), acetic acid (130 ml), conc. sulfuric acid (35 ml) and water (50 ml) was refluxed for 1.25 h, cooled to 20° C., poured over 2N NaOH/ice and extracted three times with diethyl ether (200 ml). The combined organic phases were washed with brine, dried (MgSO$_4$), and concentrated. The crude product (5.6 g, orange oil) was purified by Kugelrohr distillation (80° C., 24 mbar) yielding 2,5-dimethylcyclopentanone (4.2 g, colorless oil, 68% yield, 61% yield over 3 steps, cis/trans ratio=1:2).

d) At 0° C., a solution of 2,5-dimethylcyclopentanone (4.2 g, 0.0374 mol) in ethanol (25 ml) was added dropwise to a mixture of NaBH$_4$ (1 g, 0.0262 mol) in ethanol (25 ml). The resulting mixture was stirred for 2 h, poured over 2N HCl/ice and extracted three times with diethyl ether (100/50/50 ml). The combined organic phases were washed with brine, dried (MgSO$_4$), and concentrated to yield crude 2,5-dimethylcyclopentanol (5.0 g, colorless oil, mixture of isomers=23:9:68).

Major isomer (68%, cis, trans): $^1$H-NMR (400 MHz, CDCl$_3$) δ ppm selected signal 3.60 (dd, J=4.2, 5.7, 1H). $^{13}$C-NMR (100 MHz, CDCl$_3$) δ ppm 82.2 (d) 41.3 (d) 37.1 (d) 30.8 (t) 30.7 (t) 19.4 (q) 14.0 (q). GC/MS (EI): 114 (M$^+$, 23), 99 (4), 96 (14), 81 (37), 71 (100), 58 (70), 57 (89), 43 (27), 41 (23), 29 (10).

Second major isomer (23%, trans, trans): $^1$H-NMR (400 MHz, CDCl$_3$) δ ppm selected signal 3.03 (t, J=8.2, 1H). $^{13}$C-NMR (100 MHz, CDCl$_3$) δ ppm 86.8 (d) 41.8 (d) 29.2 (t) 18.2 (q).

GC/MS (EI): 114 (M$^+$, 27), 99 (4), 96 (14), 81 (36), 71 (100), 58 (70), 57 (87), 43 (29), 41 (22), 29 (10).

Minor isomer (9%, cis, cis): $^1$H-NMR (400 MHz, CDCl$_3$) δ ppm selected signal 3.74 (t, J=3.8, 1H). $^{13}$C-NMR (100 MHz, CDCl$_3$) δ ppm 78.9 (d) 39.9 (d) 30.2 (t) 14.3 (q). GC/MS (EI): 114 (M$^+$, 22), 99 (5), 96 (15), 81 (36), 71 (100), 58 (68), 57 (88), 43 (27), 41 (24), 29 (11).

e) A solution of crude 2,5-dimethylcyclopentanol (5.0 g, 0.0374 mol max.) and DMAP (0.46 g, 3.7 mmol) in cyclohexane (100 ml) and pyridine (5.92 g, 7.5 mmol) was treated dropwise with crotonyl chloride (6.5 g, 56.2 mmol, 90% pure). The resulting mixture was stirred for 5.5 h at 20° C., poured over aq. sat. NaHCO$_3$/ice and extracted three times with MTBE (200/100/100 ml). The combined organic phases were washed with 2N HCl, water, brine, dried (MgSO$_4$), and concentrated. Flash chromatography (SiO$_2$, hexane:MTBE 30:1) followed by Kugelrohr distillation (bp: 70° C., 0.06 mbar) of the crude product gave 2,5-dimethylcyclopentyl (E)-but-2-enoate (2.1 g, colorless oil, 31% yield over 2 steps, mixture of isomers=20:74:6).

(2S*,5S*)-2,5-dimethylcyclopentyl (E)-but-2-enoate (cis, trans; 74%): $^1$H-NMR (400 MHz, CDCl$_3$) δ ppm selected signals 6.95 (dq, J=15.4, 6.9 Hz, 1H) 5.85 (dq, J=15.4, 1.8 Hz, 1H) 4.71 (dd, J=4.3, 6.1 Hz, 1H) 1.87 (dd, J=1.8, 6.8 Hz, Me) 1.02 (d, J=7.1 Hz, Me), 0.90 (d, J=6.8 Hz, Me). $^{13}$C-NMR (100 MHz, CDCl$_3$) δ ppm 166.5 (s) 143.9 (d) 123.1 (d) 83.9 (d) 39.4 (d) 36.1 (d) 31.7 (t) 31.1 (t) 19.2 (q) 17.9 (q) 14.3 (q). GC/MS (EI): 182 (M$^+$, <1), 167 (<1), 153 (<1), 113 (2), 96 (21), 81 (20), 69 (100), 55 (11), 41 (16).

(1s*,2R*,5S*)-2,5-dimethylcyclopentyl (E)-but-2-enoate (cis, cis; 6%): $^1$H-NMR (600 MHz, BENZENE-d$_6$) δ ppm 6.95 (dq, J=15.4, 6.8 Hz, 1H) 5.83 (d, J=15.4 Hz, 1H) 5.37 (t, J=4.1 Hz, 1H) 1.80-1.88 (m, 2H) 1.57-1.77 (m, 2H) 1.39-1.46 (m, 2H) 1.33 (d, J=6.8 Hz, 3H) 0.98 (d, J=6.8 Hz, 6H). $^{13}$C NMR (150 MHz, BENZENE-d$_6$) δ ppm 165.9 (s) 143.7 (d) 123.3 (d) 80.3 (d) 39.3 (d, 2C) 31.3 (t, 2C) 17.5 (q) 14.9 (q, 2C). GC/MS (EI): 113 (M$^+$-C$_4$H$_5$O, 4), 96 (20), 81 (18), 69 (100), 55 (12), 41 (20).

(1r*,2R*,5S*)-2,5-dimethylcyclopentyl (E)-but-2-enoate (trans, trans; 20%): $^1$H-NMR (600 MHz, BENZENE-d$_6$) δ ppm 6.95 (dq, J=15.4, 6.8 Hz, 1H) 5.85 (br d, J=15.4 Hz, 1H) 4.71 (t, J=7.2 Hz, 1H) 2.04-1.97 (m, 2H) 1.64-1.71 (m, 2H) 1.33 (br d, J=6.8 Hz, 3H) 1.04 (d, J=7.2 Hz, 6H). $^{13}$C NMR (101 MHz, CDCl$_3$) δ ppm 166.2 (s) 143.9 (d) 123.5 (d) 86.9 (d) 40.5 (d, 2C) 30.4 (t, 2C) 18.5 (q, 2C) 17.5 (q).

GC/MS (EI): 113 (M$^+$-C$_4$H$_5$O, 4), 96 (20), 82 (18), 69 (100), 55 (12), 41 (20). GC/MS (EI): 113 (M$^+$-C$_4$H$_5$O, 3), 96 (26), 81 (27), 69 (100), 55 (11), 41 (18).

Odor of the mixture of isomers (20:74:6): fruity, damascone-like, plum; the odor of the all-syn isomer (6% of the mixture) was evaluated by GC-Sniff: fruity, natural, apple, damascone-like.

Example 9:
rac-(1s*,2R*,6S*)-2,6-dimethylcyclohexyl 3-(decylthio)butanoate

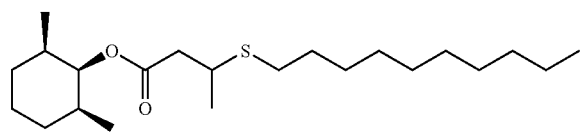 [SMILES: CCCCCCCCCCSC(C)CC(=O)O[C@@H]1[C@H](C)CCC[C@@H]1C]

To the solution of 1-dodecanethiol (9.8 g, 48.4 mmol, 0.95 equiv.) and (1s*,2R*,6S*)-2,6-dimethylcyclohexyl (E)-but-2-enoate (10.0 g, 51.0 mmol 1.0 equiv.) in THF (100 mL) was added dropwise the solution of DBU (1,8-Diazabicy-cloUndec-7-ene, 7.76 g, 51.0 mmol, 1.0 equiv.) in THF (50 mL). The resulting mixture was stirred during 22 h at RT, then poured on icecold 2 M aq. HCl-solution (100 mL). The product was extracted with MTBE and the organic layer washed with water and brine and dried over MgSO$_4$. The crude product obtained after removal of the solvents was purified by flash chromatography on SiO$_2$ (hexane/MTBE 100:1) to yield rac-(1s*,2R*,6S*)-2,6-dimethylcyclohexyl 3-(decylthio)butanoate (colourless oil, 9.87 g, 49%).

$^1$H-NMR (400 MHz, CDCl$_3$) δ ppm 0.83-0.92 (series of s, 9H), 1.19-1.25 (m, 3H), 1.27 (br. s, 12H), 1.29-1.34 (m, 7H), 1.36 (d, J=6.6 Hz, 3H), 1.38-1.46 (m, 1H), 1.54-1.69 (m, 4H), 1.70-1.78 (m, 1H), 2.44-2.52 (m, 1H), 2.54-2.59 (m, 2H), 2.67-2.74 (m, 1H), 3.16-3.32 (m, 1H), 5.07 (s, 1H). $^{13}$C-NMR (101 MHz, CDCl$_3$) δ ppm 14.12 (q), 18.44 (2q), 21.51 (q), 22.69 (t), 25.75 (2 t), 28.56 (t), 29.03 (t), 29.25 (t), 29.35 (t), 29.53 (t), 29.60 (t), 29.64 (t), 29.65 (t), 29.69 (t), 30.67 (t), 31.92 (t), 36.06 (d), 36.23 (d), 36.26 (d), 42.50 (t), 76.92 (d), 171.58 (s). EI-MS (70 ev). 398 (M+, 6), 287 (33), 229 (14), 201 (100), 111 (48), 87 (9), 69 (49), 55 (26), 41 (19).

Example 10: Selective Stability to Enzymatic Hydrolysis of Compounds of Examples 1-3

Enzymes of the nasal cavity are not easily available, but the nasal cavity contains similar enzymatic activities as found in the liver, namely carboxylesterases (J. L. Lewis, K. J. Nikula, R. Novak, A. R. Dahl, Anat Rec 1994, 239). Therefore the different compounds of examples 1-3 were compared for enzymatic hydrolysis using human liver microsomes. Chemicals were dissolved to a final concentration of 100 µM in a total volume of 600 µl of phosphate buffer (100 mM, pH 7.4, containing 1.15% potassium chloride and 1 mM of EDTA). S9 fractions from humans at a final level of 0.166 mg/ml were added (Corning® Gentest™ Human Liver S9 Pooled Donors, 20 mg/mL protein content, Product #452961;), Lot 22877,). As control experiment, equal levels of heat inactivated S9 fractions (incubated for 10 min at 99° C.) were added to parallel samples. The samples were incubated for different time periods and then mixed in 2 ml glass vials with 300 µl of Methyl-tert-butylether (MTBE) containing as internal standard 1 ppm of dodecane. Samples were extracted on a vortex mixer for 20 s, and then ca. 200 µl of the supernatant was transferred to conical GC vials and concentrated under a stream of nitrogen. 1 µl of these concentrated extracts were then injected with a splitless injection into an Agilent GC 6890N gas chromatograph equipped with a flame-ionisation detector. The following GC conditions were applied: Column: Rtx -5; 30 m length×0.32 mm internal diameter×0.25 µm film thickness; Carrier gas: Hydrogen; Column flow: 2 mL; Initial temperature of 60° C. held for 2 min, subsequent linear gradient with 10° C. per minute up to a temperature of 240° C. The peak of the test compound (parent) and the peak of potentially released alcohols after ester hydrolysis were integrated and compared to synthetic reference standards. To determine calibration curves, dilutions of the test chemicals or of the potentially released alcohols were added to heat inactivated S9 fraction and extracted, concentrated and analysed as described above. All concentrations (in test samples and calibration curves) were determined by normalization to the internal standard. FIG. 1 shows the enzymatic stability in human liver S9 fractions of the compounds of example 1-3. This graph indicates both the degradation of the parent ester and the release of the corresponding alcohol, both in heat inactivated and in active S9 fractions.

For compound in Example 1, no significant cleavage (<3%) was observed, while Example 2 is completely hydrolysed by active S9 fractions and Example 3 is significantly cleaved (15%). No cleavage in heat inactivated samples was observed clearly showing that cleavage is due to enzymatic hydrolysis.

Example 11: Skin Sensitization Test of Compounds 1 and 6a in Comparison with 3-Damascone in a Cell-Based Assay Compounds were tested using the commercial KeratinoSens™ assay for skin sensitization.

The KeratinoSens™ test compares the potential skin sensitization risk of chemicals. The KeratinoSens™ cell line contains a stable insertion of a Luciferase gene under the control of the ARE-element of the gene AKR1C2 and induction of luciferase is indicative of skin sensitization potential (R. Emter, G. Ellis, A. Natsch, Toxicol. Appl. Pharmacol. 2010, 245, 281-290). The assay was performed as described by the OECD test guideline 442d. KeratinoSens cells were grown for 24 h in 96-well plates. The medium was then replaced with medium containing the test chemical and the solvent dimethylsulfoxide (DMSO) at a final level of 1%. Each compound was tested at 12 binary dilutions in the range from 0.98 to 2000 µM. Cells were incubated for 48 h with the test agents, and then luciferase activity and cytotoxicity were determined. This full procedure was repeated three times for each chemical. For each chemical in each repetition and at each concentration, the gene induction compared to DMSO controls and the wells with statistically significant induction over the threshold of 1.5 (i.e. 50% enhanced gene activity) were determined. Furthermore, the maximal fold-induction (Imax) and the EC1.5 value (concentration in µM for induction above the threshold) were calculated. Chemicals are rated as positive (i.e. likely skin-sensitizers) in the assay if the following three criteria are fulfilled:

(i) EC1.5 value is below 1000 µM.
(ii) At the lowest concentration with a gene induction above 1.5 fold, the cellular viability is above 70%.

(iii) There is an apparent overall dose-response for luciferase induction, which is similar between the repetitions.

(1s*,2R*,6S*)-2,6-dimethylcyclohexyl (E)-but-2-enoate, the compound of Example 1, and (1S*,2S*)-2,6,6-trimethylcyclohex-3-en-1-yl (E)-but-2-enoate, the compound of Example 6a were compared with β-Damascone.

Figures 2A, 2B:
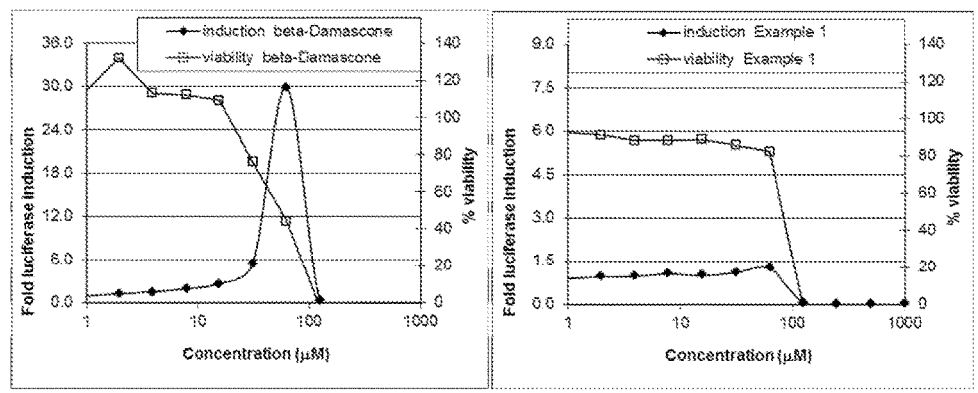
FIG. 2a depicts the gene-induction and cell viability curves for 6-Damascone.
FIG. 2b illustrates the corresponding data for compound of Example 1, including the induction of luciferase activity and cellular viability.

FIG. 2a shows the gene-induction and cell viability curves for β-Damascone and FIG. 2b the corresponding data for compound of Example 1, in which the black diamonds indicate the induction of the luciferase activity and the open squares Cellular viability, respectively.

The compound of Example 1 does not induce luciferase activity above the 1.5-fold threshold, and is thus rated as non-sensitizing by this assay. β-Damascone on the other hand clearly induces the luciferase gene already at a concentration of 4.5 micromolar, indicating it is a significantly sensitizing compound. These results show that Example 1 can be used in perfume formulations for reduced sensitization risk to the consumer. Similar data have been obtained for the compound of Example 6a.

Table 1 shows the results of compounds according to this disclosure, as compared with β-Damascone. The maximal gene induction was below the threshold of 1.5-fold for the inventive compounds, while the maximal gene induction was at 29.8-fold for β-Damascone.

TABLE 1

|  | Imax (fold maximal gene induction) | Concentration for 1.5-fold gene induction (EC 1.5 in μM) | Concentration for 50% Cytotoxicity (in μM) |
| --- | --- | --- | --- |
| β-Damascone | 29.8 | 4.5 | 56.73 |
| Compound of Example 1 | 1.25 | No induction | 86.9 |
| Compound of Example 6a | 1.13 | No induction | 89.4 |

Example 12: Skin Sensitization Test of Compound 1 in Comparison with Damascones in a Peptide Reactivity Assay A second method to determine allergenic potential of chemicals is the DPRA direct peptide assay (OECD TG 442c). It is based on the fact that allergenic chemicals must react with a peptide/protein in order to be immunogenic.

A peptide reactivity assay (A. Natsch, H. Gfeller, Toxicol. Sci. 2008, 106, 464-478) was conducted similarly to the DPRA assay, but including a kinetic measurement to quantify reactivity: The test chemicals were dissolved to a final concentration of 4 mM in acetonitrile and 250 μl of this solution were added to 2 ml HPLC vials. The test peptide Cor1C-420 with the sequence Ac-NKKCDLF (Genscript Inc., Piscataway, N.J., USA), was dissolved at 0.133 mM in 20 mM phosphate buffer at pH 7.5, and 750 μl of this solution were added to each test vial (final concentrations: 1 mM of test chemical and 0.1 mM of peptide in 25% acetonitrile; ratio 1:10 as in the DPRA assay). The samples were incubated for 1-24 h at 37° C. and at regular intervals they were analysed by LC-MS analysis on a VELOS PRO Mass spectrometer (Thermo SCIENTIFIC, San Jose, Calif., U.S.A.) operated in the ESI(+) mode.

Mass spectra were recorded from 200-2000 amu. A ZORBAX Eclipse XDB-C18 column, 2.1 mm ID, 150 mm, 5-Micron (Agilent Technologies) was used. The mobile phase consisted of H2O (A) and methanol (B) each containing 0.1% formic acid (v/v). The solvent flow was 250 μl/min and the following gradient (ratio A:B) was used: 0 min, 95:5; 2 min, 40:60; 10 min, 2:98; 12 min, 2:98. The integration was performed with Xcalibur Quan Browser™

Figure 4:
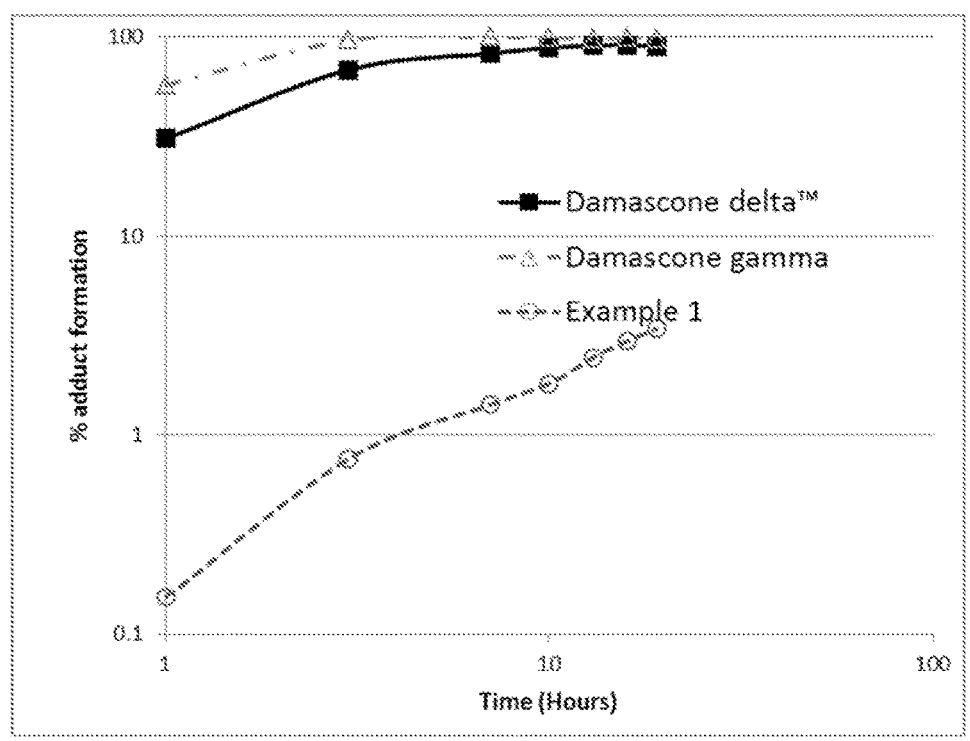
FIG. 4 depicts a result of a peptide reactivity assay according to Example 12, namely the formation of modified peptides.

Two endpoints are measured with this assay:

a) Depletion of the parent peptide (FIG. 3): The mass of the protonated parent peptide is measured and the corresponding peak integrated (% depletion). Depletion of the parent peptide is indicative of reactivity and is described as endpoint in OECD guideline 442c.

b) Formation of modified peptides (FIG. 4): The specific ion trace for a new adduct with the mass of the test chemical added to the test peptide is extracted, and the peak of the peptide-adduct is integrated. Peptide adduct formation is a particular sensitive endpoint to determine reactive, and thus allergenic nature of compounds.

Figure 3:
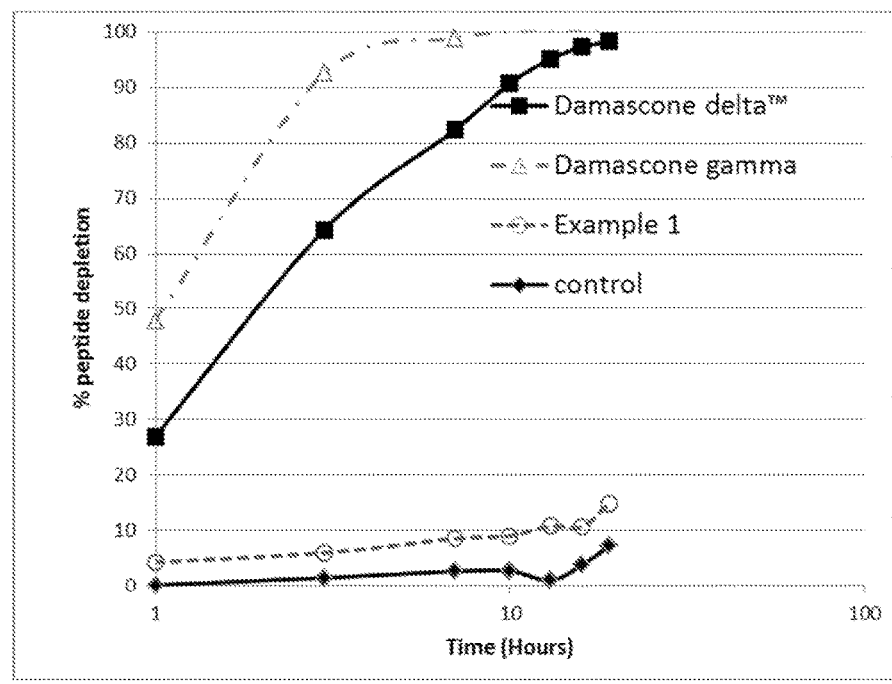
FIG. 3 depicts a result of a peptide reactivity assay according to Example 12, namely the depletion of a parent peptide.

FIGS. 3 (peptide depletion) and 4 (adduct formation on a logarithmic scale) compare the peptide reactivity of two commercial damascones with the compound of Example 1 ("Example 1"). After 1 h, Example 1 produces >100 lower levels of peptide adducts as compared to Damascone Delta™ and Damascone gamma, indicating a dramatic and unexpected reduction of reactivity (and thus allergenicity) for Example 1. Peptide depletion indicates complete consumption of the peptide by Damascones, while only <10% is consumed as compared to controls for the Example 1.

Example 13: Perfume Example 1: A Freshly Cut Ginger Root Perfume for Shampoo Application (0.5% in Shampoo Base)

| CAS-No. | Compound/Ingredient | parts by weight |
| --- | --- | --- |
| 150-84-5 | ACET CITRONELLYLE | 60 |
| 105-87-3 | ACET GERANYLE SYNT | 20 |
| 112-31-2 | ALD C 10 DECYLIQUE | 3 |
| 507-70-0 | BORNEOL CRYSTALS | 10 |
| 5392-40-5 | CITRAL LEMAROME N | 100 |
| 68917-33-9 | CITRON TERPENES w/o CITRAL | 100 |
| 65405-70-1 | DECENAL-4-TRANS | 1 |
| 8023-89-0 | ELEMI ESS | 30 |
| 10339-55-6 | ETHYL LINALOL | 40 |
| 470-82-6 | EUCALYPTOL NATURAL | 20 |
| 106-24-1 | GERANIOL 980 | 120 |
| 24851-98-7 | HEDIONE | 300 |
| 97-54-1 | ISOEUGENOL | 20 |
| 78-70-6 | LINALOL SYNT | 100 |
| 68855-99-2 | LITSEA CUBEBA ESS CHINE | 15 |
| 67674-46-8 | METHYL PAMPLEMOUSSE | 30 |
| 121-33-5 | VANILLIN @10% TEC | 1 |

|  | R1 | F2 | F3 |
| --- | --- | --- | --- |
| DIPROPYLENE GLYCOL | 30 | 0 | 0 |
| Compound A | 0 | 30 | 0 |
| Compound B | 0 | 0 | 30 |
|  |  |  | 1000 |

Compound A: (1s*,2R*,6S*)-2,6-dimethylcyclohexyl (E)-but-2-enoate
Compound B: mixture of (1s*,2R*,6S*)-2,6-dimethylcyclohexyl (E)-but-2-enoate, (2R*,6R*)-2,6-dimethylcyclohexyl (E)-but-2-enoate and (1r*,2R*,6S*)-2,6-dimethylcyclohexyl (E)-but-2-enoate in a ratio of 72:18:8.

The reference accord R1 comprising dipropylene glycol (DPG), but no compounds A or B gives a freshly cut ginger root impression, mainly through a citrus citral freshness combined with aromatic elements. Formula F2, wherein DPG is replaced by compound A, softens the sharp citral freshness with a juicy natural fruityness, damascone like character that complements nicely the accord and reinforces the natural ginger root connotation. Formula F3, wherein DPG is replaced by compound B, does also cover the sharp citral freshness, but adds a green chemical plastic and dusty connotation, which is not pleasant and natural anymore.

Example 14: Perfume Example 2: A Fruity Plum, Red Berry Perfume for Shampoo Application, (0.5% in Shampoo Base)

| CAS-No. | Compound/Ingredient | parts by weight | | | |
|---|---|---|---|---|---|
| 123-86-4 | ACET BUTYLE | 15 | | | |
| 103-54-8 | ACET CINNAMYLE | 20 | | | |
| 21722-83-8 | ACET CYCLOHEXYLE ETHYLE | 15 | | | |
| 105-87-3 | ACET GERANYLE SYNT | 30 | | | |
| 3681-71-8 | ACET HEXENYLE-3-CIS | 1 | | | |
| 142-92-7 | ACET HEXYLE | 25 | | | |
| 100-52-7 | BENZALDEHYDE @10% TEC | 6 | | | |
| 10094-34-5 | BUTYRATE DIMETHYL BENZ CARB | 440 | | | |
| 123-68-2 | CAPRONATE ALLYLE | 2 | | | |
| 706-14-9 | DECALACTONE GAMMA | 3 | | | |
| 106-24-1 | GERANIOL 980 | 15 | | | |
| 8013-90-9 | IONONE BETA | 30 | | | |
| 103-60-6 | ISOBUTYRATE PHENOXYETHYLE | 300 | | | |
| 78-70-6 | LINALOL SYNT | 30 | | | |
| 118-71-8 | MALTOL LG CRIST 1%/AB | 10 | | | |
| 7452-79-1 | METHYL-2-BUTYRATE ETHYLE | 3 | | | |
| 104-67-6 | PECHE PURE | 10 | | | |
| 104-61-0 | PRUNOLIDE | 4 | | | |
| 5471-51-2 | RASPBERRY KETONE (N112) | 10 | | | |
| 121-33-5 | VANILLIN | 1 | | | |
| | | | R4 | F5 | F6 |
| | DIPROPYLENE GLYCOL | | 30 | 0 | 0 |
| | Compound A | | 0 | 30 | 0 |
| | Compound B | | 0 | 0 | 30 |
| | | | | | 1000 |

Compound A: (1s*,2R*,6S*)-2,6-dimethylcyclohexyl (E)-but-2-enoate
Compound B: mixture of (1s*,2R*,6S*)-2,6-dimethylcyclohexyl (E)-but-2-enoate, (2R*,6R*)-2,6-dimethylcyclohexyl (E)-but-2-enoate and (1r*,2R*,6S*)-2,6-dimethylcyclohexyl (E)-but-2-enoate in a ratio of 72:18:8.

The reference accord R4 comprising dipropylene glycol (DPG), but no compounds A or B represents a fruity berry combo, mainly between plum and raspberry. Formula F5, containing compound A instead of DPG, shifts the juicy pear freshness to a harmonized plum berry juiciness, having a natural and edible effect. Formula F6, wherein DPG is replaced by compound B, moderates the pear like freshness, but adds a green chemical plastic dusty character and became unpleasant and not natural.

The invention claimed is:
1. A compound of formula I

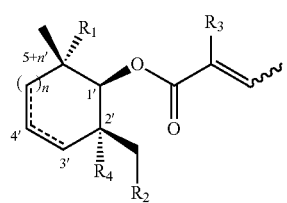

formula I wherein $R_1$, $R_2$, $R_3$ and $R_4$ can be independently selected from H or Me, n=0, 1, the dotted lines are indicating single bonds, or in case n=0 an isolated double bond at position 3', or in case n=1 an isolated double bond at position 3' or 4', and the wavy bond is indicating an unspecified configuration of the adjacent double bond.

2. A compound according to claim 1 selected from the group consisting of
(1s*,2R*,6S*)-2,6-dimethylcyclohexyl (E)-but-2-enoate,
(1s*,2R*,6S*)-2,6-dimethylcyclohexyl (E)-2-methylbut-2-enoate,
(1R*,2S*,6R*)-2-ethyl-6-methylcyclohexyl (E)-but-2-enoate,
(1S*,2S*)-2,6,6-trimethylcyclohex-3-en-1-yl (E)-but-2-enoate,
(1R*,2S*,6R*)-2,6-dimethylcyclohex-3-en-1-yl (E)-but-2-enoate and
(1s*,2R*,5S*)-2,5-dimethylcyclopentyl (E)-but-2-enoate.

3. A fragrance composition comprising a compound according to claim 1, or a mixture thereof.

4. A fragrance composition according to claim 3 comprising at least one other fragrance ingredient.

5. A consumer product comprising a compound according to claim 1 or a fragrance composition according to claim 3, and a consumer product base.

6. A consumer product according to claim 4 selected from fine perfumery, household products, laundry products, body care products, cosmetic and air care products.

7. A method of improving, enhancing or modifying a consumer product by means of addition thereto of an olfactory acceptable amount of a compound of formula I as defined in claim 1.

8. A precursor adapted to generate a compound according to formula (I) as defined in claim 1, having the formula (II)

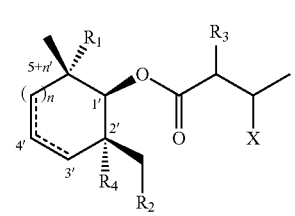

formula II in which
$R_1$, $R_2$, $R_3$ and $R_4$ can be independently selected from H or Me,
n=0, 1,
the dotted lines are indicating single bonds, or in case n=0 an isolated double bond at position 3', or in case n=1 an isolated double bond at position 3' or 4', the substituents at the ring system are having an all-syn relationship, and in which X is selected from $SR^5$, $NHR^8$ and $NR^6R^7$, $R^5$, $R^6$ and $R^7$ being selected from linear or branched $C_1$-$C_{15}$ alkyl, a $C_3$-$C_8$ cycloalkyl or an aryl substituent, both optionally substituted with linear or branched $C_1$-$C_7$ alkyl groups or, in the case of $NR^6R^7$, $R^6$ and $R^7$, together with the nitrogen atom to which they are attached, form part of a polymeric entity.

* * * * *